United States Patent [19]
Cannon, III

[11] 3,942,533
[45] Mar. 9, 1976

[54] CARDIAC DEFIBRILLATOR DEPOLARIZING PADDLE ARRANGEMENT

[76] Inventor: Robert L. Cannon, III, 17 Lakeview Terrace, Waltham, Mass. 02154

[22] Filed: Oct. 17, 1974

[21] Appl. No.: 515,727

[52] U.S. Cl............................ 128/417; 128/419 D
[51] Int. Cl.²........................................... A61N 1/18
[58] Field of Search ....... 128/417, 419 D, 404, 405, 128/406, 418

[56] References Cited
UNITED STATES PATENTS

| | | |
|---|---|---|
| 3,163,166 | 12/1964 | Brant et al. .......................... 128/405 |
| 3,467,863 | 9/1969 | Karsh .............................. 128/419 D |
| 3,702,613 | 11/1972 | Panico et al. .................. 128/419 D |
| 3,762,420 | 10/1973 | Moore et al. ................... 128/419 D |
| 3,826,245 | 7/1974 | Funfstuck ...................... 128/419 D |
| 3,830,229 | 8/1974 | Johnson ............................. 128/417 |

Primary Examiner—Robert W. Michell
Assistant Examiner—Lee S. Cohen
Attorney, Agent, or Firm—H. R. Berkenstock, Jr.; William C. Nealon

[57] ABSTRACT

A cardiac defibrillator paddle in which the elctrode surface is provided with a removable cap. This permits the electrode to have its conductive paste pre-applied, with the cap readily removable for immediate use.

1 Claim, 3 Drawing Figures

U.S. Patent    March 9, 1976    3,942,533

CARDIAC DEFIBRILLATOR DEPOLARIZING PADDLE ARRANGEMENT

BACKGROUND OF THE INVENTION

The present invention is related to cardiac defibrillator apparatus, and in particular to the electrode paddles which are a part of such defibrillator apparatus.

A defibrillator electrode paddle is a device which is useful with a second similar electrode paddle for applying a controlled electrical shock across the heart of a human patient to terminate fibrillation thereof when the heart is in a condition of arrhythmia. These paddles are typically of a disc-like configuration mounted on a coaxial and elongated handle.

The two electrode paddles are generally coated with a thick layer of conductive paste or electrolyte in order to optimize the electrical connection between the paddle and the chest of a patient. The paddles are then applied with firm pressure on the chest wall and an electrical discharge passed therethrough.

Prior to using a defibrillator apparatus in this manner, one of the major causes of delay is the need to apply the conductive paste to the electrode surface prior to application to the body. Certain patents of which Applicant is now aware and which may relate to Applicant's invention, but which do not disclose nor suggest Applicant's invention, include U.S. Pat. Nos. 3,467,863 to Karsh, 3,224,447 to Becker et al., 3,151,619 to Sullivan, and 2,555,037 to Jensen.

SUMMARY OF THE INVENTION

Briefly, the present invention includes a defibrillator electrode paddle having provision for a removable cap over its electrode surface. Within this cap, and on the electrode surface, is stored conductive paste. When the defibrillator is required for use, the electrode caps are easily and quickly removed and the electrode paddles, having been precoated, are immediately ready for use.

It is an object of the present invention to provide defibrillator electrode paddles which enable the conductive paste to be pre-applied and stored with the electrode paddle for emergency use.

Other objects, advantages and features of the present invention will become apparent from the following description thereof, taken in connection with the accompanying drawing.

DRAWING

DETAILED DESCRIPTION OF PREFERRED EMBODIMENT

Figure 1:
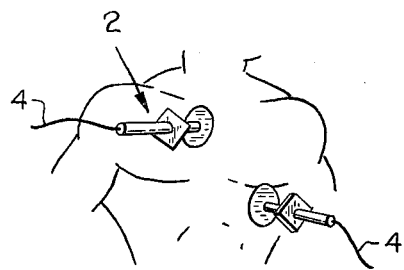
FIG. 1 is a view showing the environment of defibrillator electrode paddle in association with a human patient.

Referring now to FIG. 1, a human patient is represented against whose chest are placed two similar defibrillator electrode paddles 2. Electrode paddles 2 are connected by suitable electric lead wires 4 to a defibrillator apparatus, not shown.

Figure 2:
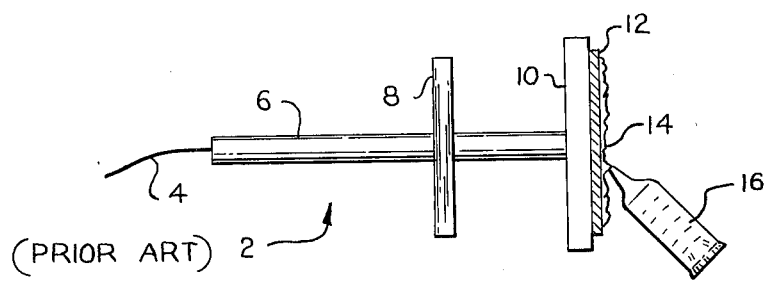
FIG. 2 is a side view, partly in section, of a typical defibrillator electrode paddle according to the prior art.

Referring now to FIG. 2, electrode paddle 2 is shown in more detail which includes an insulation handle member 6 covering lead wire 4, a flange 8 to limit hand travel, and an end flange 10 before an electrode face 12 is exposed. In the use of this apparatus and at the point of use, a thick layer of electrically-conductive paste 14 must be applied to the face of electrode 12 from a container 16 in a somewhat time-consuming operation.

Figure 3:
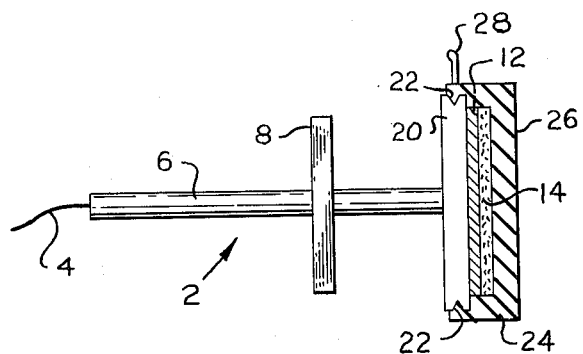
FIG. 3 is a similar view of an electrode paddle according to the present invention.

Referring now to FIG. 3, wherein like numbers designate like elements, electrode paddle 2 includes an end flange 20 which has been modified by the addition thereto of an annular or peripheral groove 22. Annular groove 22 is formed to accommodate a mating flange 24 which projects from a cup-like cover or cap member 26. The cap and paddle members are thus positively keyed together. Cap member 26 is of a depth sufficient to embrace end flange 20, fitting into annular groove 22 thereof, and to cover electrode face 12, leaving a space or volume adjacent the electrode 12 for the accommodation of conductive paste 14. Cap member 26 is made of a flexible material such as plastic and is readily removable from end flange 20. To facilitate this, cap member 26 may be provided with a tab member 28 for easier gripping.

In alternative embodiments, the mating key arrangement at 22 and 24 might be disposed on opposite members. That is, the groove might be located in flange 24 instead of in flange 20. Again, it would be possible to have the mating key arrangement located between electrode 12 and cap 26 rather than between end flange 20 and cap 26. Furthermore, the cap 26 might be a relatively rigid piece with the periphery of flange 20 being resilient.

In the use of the present invention, a suitable amount of conductive paste 14 is placed within cap member 26. Cap 26 is then fastened to the electrode paddle 2 which can then be stored for future use. At such time as the paddle is required in use, it is immediately available by simply disengaging cap member 26. There might be two general classes of defibrillator cap 26, these being related to the type of fit relative to the associated paddle. In one class, a relatively tight or sealing fit will be necessary to prevent the possible drying out of the electrolyte. A second cap which has a less critical fit may be used where its function is only to contain an electrolyte which is formulated to be non-drying.

It will be apparent that a defibrillator electrode paddle arrangement has been provided here which facilitates its emergency use by permitting storage therwith of the conductive paste which heretofore has been manually applied at the time and place of use.

It may occur to others to make modifications of the present invention which will lie within the concept and scope thereof and not constitute a departure therefrom. Accordingly, it is intended that the present invention be not limited by the details in which it has been described but that it encompass all within the purview of the following claims.

What is claimed is:

1. At least one cardiac defibrillator electrode paddle conductive paste storage system comprising:
   an insulating handle suitable for grasping;
   an end flange connected to said handle at one end thereof, said end flange being configured with peripheral key means,
   an electrode face mounted on a side of said end flange opposite to said handle, said face covering a substantial portion of said side;
   a resilient and reusable cover member peripherally configured with the complement of said key means to permit tight-fit removable mounting of said cover member to said end flange, said cover member being removably connected with said end flange and together defining a sealed space between said electrode face and the inside surface of said cover member;

conductive fluid stored in said sealed space whereby the orientation of said at least one paddle is not critical to the storage of said conductive fluid and whereby the distance between said stored conductive fluid of one of said at least one paddle and said stored conductive fluid of another of said at least one paddle is not necessarily a fixed distance;

another flange connected to said handle at a predetermined distance from said end flange to limit travel of said handle grasping towards said end flange;

means for electrically connecting said electrode face to a power source and for electrically insulating said handle and said another flange from said electrode face;

and tab means protruding from said cover member for facilitating removal of said cover member and exposure of said conductive fluid.

\* \* \* \* \*